United States Patent [19]

Müller

[11] Patent Number: 4,629,773

[45] Date of Patent: Dec. 16, 1986

[54] IMIDYLCOMPOUNDS, POLYMERS THEREFROM, AND USE OF THE POLYMERS

[75] Inventor: Beat Müller, Marly, Switzerland

[73] Assignee: Ciba-Geigy Corporation, Ardsley, N.Y.

[21] Appl. No.: 724,426

[22] Filed: Apr. 18, 1985

Related U.S. Application Data

[62] Division of Ser. No. 405,472, Aug. 5, 1982, Pat. No. 4,532,332.

[30] Foreign Application Priority Data

Aug. 17, 1981 [CH] Switzerland ............ 5303/81

[51] Int. Cl.$^4$ ............................................. C08F 22/40
[52] U.S. Cl. .................................... 526/262; 430/270; 528/322

[58] Field of Search ......................................... 526/262

[56] References Cited

U.S. PATENT DOCUMENTS

| | | |
|---|---|---|
| 4,079,041 | 3/1978 | Baumann et al. |
| 4,163,097 | 7/1979 | Baumann et al. ................. 526/262 |
| 4,242,264 | 12/1980 | Zweifel et al. ..................... 526/262 |
| 4,532,332 | 7/1985 | Müller . |

Primary Examiner—Edward J. Smith
Attorney, Agent, or Firm—Luther A. R. Hall

[57] ABSTRACT

There are obtained from N-(hydroxypolyoxaalkylene)imidyl compounds and (meth)acrylic acid esters thereof homopolymers or copolymers with olefinically unsaturated comonomers. These polymers are photosensitive and are suitable as photographic recording material, as adhesives and as agents for surface coating.

8 Claims, No Drawings

IMIDYLCOMPOUNDS, POLYMERS THEREFROM, AND USE OF THE POLYMERS

This is a divisional of application Ser. No. 405,472, filed on Aug. 5, 1982, now U.S. Pat. No. 4,532,332, issued on July 30, 1985.

The present invention relates to imidyl compounds having hydroxyl or ethenyl groups as functional groups, to homo- or copolymers therefrom, and to their use as photographic recording material.

The importance of photosensitive polymers has constantly increased in industry, particularly in the production for example of printed circuits and printing plates. A requirement with regard to these photopolymers is that they can be economically processed. The development capacity of the polymers crosslinked by exposure to light is determined principally by the layer thickness, and by the development time and temperature, which have to be not too long and not too high, respectively, if processing is to be profitable. The mechanical stressing during processing renders necessary also good adhesion on the substrate, especially in the case of greater layer thicknesses. It is moreover a favourable factor in processing when a certain tolerance is provided with respect to development, so that the desired result is not dependent on the strict obervance of critical limiting values.

In the German Offenlegungsschriften Nos. 2,626,795 and 2,626,769 are described imidyl compounds and copolymers therefrom, which can be used as photographic recording material. There are also described, inter alia, N-(hydroxyethyl)-dimethylmaleimide and N-($\beta$-hydroxypropyl)dimethylmaleimide, acrylic esters and methacrylic esters thereof and copolymers formed therefrom. Tests however have shown that it is possible only within narrow limits of the development conditions to obtain a satisfactory image quality, and that outside these limits there is observed either the formation of fog or a swelling of the crosslinked polymer. Also the adhesion of the photocrosslinkable polymer layer on the substrate, especially with greater layer thicknesses, is not adequate.

It is the object of the present invention to provide imidyl compounds for photopolymerisable polymers, which, as photographic recording material, exhibit, within wider development limits, no fog formation and swelling, even in the case of greater layer thicknesses, and which adhere better to the substrate.

The present invention thus relates to imidyl compounds or mixtures of imidyl compounds of the formula I

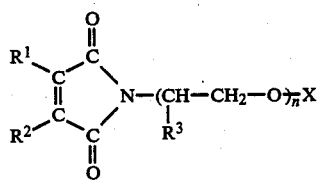

(I)

wherein
  $R^1$ and $R^2$ independently of one another are $C_1$–$C_4$-alkyl, or
  $R^1$ and $R^2$ together are tri- or tetramethylene which is unsubstituted or substituted by $C_1$–$C_4$-alkyl,
  $R^3$ is a hydrogen atom or $C_1$–$C_4$-alkyl,
  n is a number from 2 to 30, and
  X is a hydrogen atom or $CO-CR^4=CH_2$, in which
    $R^4$ is a hydrogen atom or methyl.

Preferred among the mixtures of imidyl compounds are those in which n is various numbers from 2 to 30. Preferably, however, n is a number from 2 to 20, especially 2 to 10, and in particular 2 to 6.

As alkyl, $R^1$ and $R^2$ can be methyl, ethyl, propyl, i-propyl, n-butyl, i-butyl and t-butyl. The alkyl substituents can have the same meaning when $R^1$ and $R^2$ together are tri- or tetramethylene. The trimethylene or tetramethylene is preferably monoalkylated, and the alkyl substituent is preferably methyl. $R^1$ and $R^2$ are each preferably methyl, and together unsubstituted or methylated 1,4-butylene.

As alkyl, $R^3$ can be for example methyl, ethyl, n-propyl or n-butyl. The preferred meaning of $R^3$ is methyl, and particularly a hydrogen atom.

A preferred group of compounds of the formula I are those of the formula

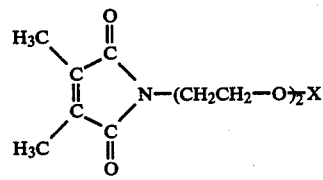

wherein X has the meaning defined in the foregoing.

The compounds of the formula I can be produced, using analogous processes according to German Offenlegungsschrift No. 2,626,795, by reacting at least stoichiometric amounts of poly(oxyalkylene)amine of the formula II

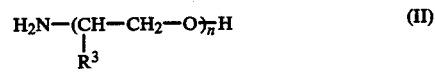

(II)

with a dicarboxylic acid anhydride of the formula III

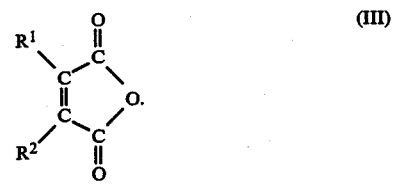

(III)

The reaction is performed advantageously at temperatures of 50° to 200° C., preferably at 70° to 150° C., in the presence of an inert solvent, by means of removal by distillation of the formed reaction water. In another embodiment for producing compounds of the formula I wherein X is H, the procedure is such that optionally $C_1$–$C_4$-alkylated ethylene oxide is added, by an addition reaction, to imidyl compounds in which X in the formula I is hydrogen, and n is the number 1 or a number >1. To produce compounds of the formula I wherein X is methacryloyl or acryloyl, the alcohols of the formula I can be esterified with (meth)acrylic acid or with ester-forming derivatives thereof, for example with acid halides, esters and anhydrides.

Suitable solvents are for example: ethers, such as diethyl ether, dibutyl ether, tetrahydrofuran and dioxane, and hydrocarbons, such as pentane, cyclohexane, benzene, toluene and xylene.

The poly(oxyalkylene)amines of the formula II are known, and can be produced, using processes known per se, by reaction of optionally $C_1$-$C_4$-alkylated, N-protected aminoethanols with $(n-1)$ mols of an optionally $C_1$-$C_4$-alkylated ethylene oxide.

The anhydrides of the formula III are known.

Depending on the magnitude of the numerical value of n, the compounds of the formula I are of a liquid, viscous to resinous consistency. They are particularly suitable for the production of photocrosslinkable homo- and copolymers which are excellent photographic recording materials.

Further subject matter of the present invention is formed by photosensitive, crosslinkable homopolymers from compounds of the formula I and copolymers thereof with ethylenically unsaturated comonomers. The polymers can have a mean molecular weight of 1000 to 1,000,000, preferably 5000 to 500,000.

Depending on the purpose of application, the copolymers according to the invention can contain the photosensitive compounds of the formula I in an amount of 1 to 99% by weight, preferably 5 to 95% by weight, and particularly 20 to 90% by weight, and the comonomers in a amount of 99 to 1% by weight, preferably 95 to 5% by weight, and especially 80 to 10% by weight, relative to the polymer. The desired range of properties of the copolymer can be obtained by using one or more compounds of the formula I and comonomers for producing the copolymers. Suitable comonomers are for example: α-olefins, such as ethylene, propylene, n-butylene, isobutylene, pentylene and hexylene, vinyl halides, such as vinyl chloride, vinyl bromide, vinyl fluoride, tetrafluoroethylene and vinylidene chloride, aromatic vinyl compounds, such as styrene, methylstyrene, vinyltoluene or α-chlorostyrene, heterocyclic vinyl compounds, such as vinylpyrrolidone, vinylcarbazole, vinylpyridine, vinylimidazole, vinyl ketones, such as methylvinyl ketone, vinyl esters, such as vinyl acetate, vinyl ethers, such as vinylmethyl ether, vinylsulfonic acids, allyl compounds and vinylglycidyl ethers, and also optionally dienes, such as butadiene, chlorobutadiene, isoprene or chloroprene.

A preferred group of vinyl monomers are: the α,β-unsaturated carboxylic acids and derivatives thereof, for example acrylic acid, methacrylic acid, crotonic acid, maleic acid or fumaric acid, dicarboxylic acid anhydrides, such as maleic anhydride, α,β-unsaturated nitriles, such as acrylonitrile, methacrylonitrile, crotonitrile, α,β-unsaturated carboxylic acid amides, such as acrylic acid amide, methacrylic acid amide, crotonic acid amide and α,β-unsaturated carboxylic acid esters, such as methacrylate, ethyl acrylate, propyl acrylate, butyl acrylate, pentyl acrylate, hexyl acrylate, octyl acrylate, 2-ethylhexyl acrylate, isopropyl acrylate, isobutyl acrylate and the analogous methacrylic acid esters and crotonic acid esters.

A particularly preferred subgroup consists of copolymers formed from compounds of the formula I with acrylic acid, methacrylic acid, acrylic acid esters and/or methacrylic acid esters. The compounds of the formula I are contained preferably in an amount of 40 to 90% by weight, especially 60 to 90% by weight, the acrylic and methacrylic acid in an amount of 5 to 20% by weight, preferably 5 to 30% by weight, and the acrylic acid and methacrylic acid esters in an amount of 5 to 20% by weight, preferably 5 to 30% by weight, relative to the polymer.

The polymers according to the invention can be produced by known synthesis methods for the production of macromolecules having photoactive, side-chain groups. Processes of this kind are described for example in the German Offenlegungsschrift No. 2,626,769. Basically, the following methods are suitable:

1. incorporation of compounds of the formula I in which X is hydrogen into an existing polymer chain; and
2. build-up of the polymer chain by unipolymerisation of compounds of the formula I in which X is (meth)acryloyl, or copolymerisation with comonomers.

It is possible to obtain by both procedures in part the same products. The hydroxyl group in the compounds of the formula I can also be converted, for use in the first procedure, into suitable derivatives with other reactive groups, for example into dicarboxylic acid half-esters, —COCl and glycidyl ethers.

If the photosensitive compounds of the formula I or suitable derivatives are incorporated, by a secondary reaction, into an already existing polymer chain, this incorporation is effected either by a condensation reaction with the removal of $H_2O$, alkoxy, hydrogen halide, or the like, or by an addition reaction with simultaneous opening of a ring system, for example of a dicarboxylic acid anhydride group or of an epoxide group.

Suitable starting polymers for the introduction of the photosensitive compounds of the formula I by condensation or by addition are for example the following products: polyacrylic acid, polymethacrylic acid and esters thereof, copolymers formed from these acids and other ethylenically unsaturated monomers, copolymers, built up from maleic anhydride and ethylenically unsaturated monomers, such as methylvinyl ether, ethylene, styrene, hexene-1, decene-1, tetracene-1 and octadecene-1, polymers having free hydroxyl groups, such as uni- or copolymers of acrylic acid- and methacrylic acid hydroxyalkyl esters, polyvinyl alcohols, polymers having free glycidyl groups, such as copolymers based on acrylic and methacrylic acid glycidyl esters, and polyvinyl glycidyl ether.

Polymerisation according to the second method can be performed by means of radical catalysis, preferably in solution, without in the process premature crosslinking reactions being observed. The reaction conditions, for example quantity ratios, temperature, catalysts, solvents, and such like, are described in detail in the German Offenlegungsschrift No. 2,626,769. The polymers can be isolated by customary processing methods, for example by precipitation from the solution, or by removal of the solvent by distillation.

The polymers according to the invention are suitable for various applications. By virtue of the photosensitive maleimide groups present, they are suitable in particular for crosslinking under the influence of electromagnetic waves, with crosslinking then leading to insoluble products. It is thus possible to obtain relief images by means of image-wise exposure and subsequent development (dissolving out of the unexposed, uncrosslinked polymer component). In addition to being used as photographic recording material, the polymers according to the invention can be used as adhesives and for the surface protection of various substrates, such as plastics, metals, glass, wood and ceramics. It is necessary when the polymers are used as adhesives for at least one substrate to be transparent.

Customary additives which do not unfavourably affect the photosensitivity can be incorporated into the polymers. Examples of such additives are in particular sensitisers, such as are described for example in the German Offenlegungsschrift No. 2,626,769, and also matting agents, levelling agents, fillers, fire-proofing agents, optical brighteners, antioxidants, light stabilising agents and processing stabilisers.

The photosensitive layer can be applied to suitable substrates or carriers by customary methods, such as dipping and spraying processes, and centrifugal, cascade and curtain coating.

The application possibilities for the polymers according to the invention are, for example, in the fields of photomanufacture, printing plates and non-silver photography. In the case of non-silver photography, the polymer image which is scarcely to very poorly visible after exposure and development, can be rendered clearly visible by being coloured with oil-soluble dyes or, when the polymer contains acid groups, such as carboxylic acid groups, by being coloured with cationic dyes.

The photographic recording material is especially suitable for producing photographic masks for the electronics industry, for textile printing and for the printing trade.

The polymers according to the invention are distinguished by good adhesion. As photographic recording material, they display a very high image quality, also with greater layer thicknesses. At higher bath temperatures, there is obtained, even with short development contact times, a complete development of the image, and with longer contact times no swelling of the exposed polymer parts is observed. A longer contact time for development is required with falling temperature. It is of particular advantage that the development conditions can be selected to ensure that process variations have no unfavourable effect on the good quality of the image.

The following Examples further illustrate the invention.

EXAMPLE 1

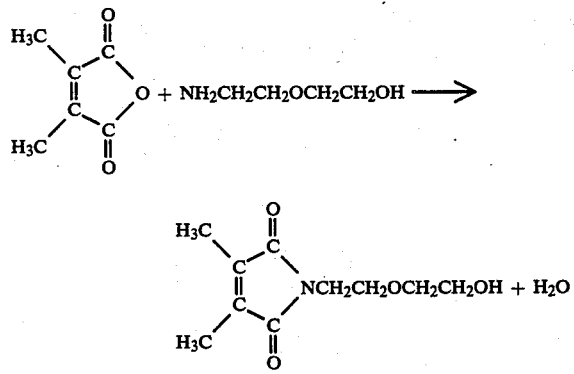

63.05 g (0.5 mol) of dimethylmaleic acid anhydride are placed into 250 ml of toluene in a three-necked flask fitted with stirrer, thermometer and water separator, and 53.61 g (0.51 mol) of diglycolamine are added during 10 minutes. The mixture is subsequently refluxed for 1 hour, in the course of which about 9 ml of water are separated. In order to remove the excess diglycolamine, 5 g of an acid ion-exchange resin are added, and the mixture is stirred for 10 minutes; the mixture is then cooled, and the ion-exchange resin is filtered off. The product is pure to the extent of more than 98% (gas-chromatographic determination). After removal of the toluene, the product is distilled off; boiling point: 145° C./0.5 mm/Hg; yield 95%. The NMR spectrum is in agreement with the structure.

| Analysis: | calculated | found |
|---|---|---|
| % C | 56.33 | 56.11 |
| % H | 7.09 | 7.23 |
| % N | 6.57 | 6.66 |

EXAMPLE 2

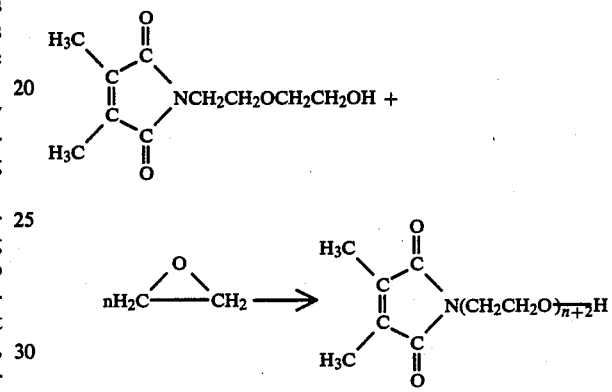

2.6 ml of freshly distilled boron trifluoride etherate are added to 263 g of the dimethylmaleic acid imidyl alcohol according to Example 1, and there are introduced at 70°–80° C., with vigorous stirring, 101 g of ethylene oxide in the course of 1½ hours. The reaction mixture is fractionally distilled, and five different fractions can be separated (n=2,3,4,5,6).

| Boiling point | Pressure | Product with n being | Amount |
|---|---|---|---|
| 125–126° C. | 0.02 | 2 | 80 g |
| 150–153° C. | 0.005 | 3 | 74 g |
| 191–192° C. | 0.004 | 4 | 100 g |
| 212° C. | 0.003 | 5 | 54 g |
| 250° C.[1] | 0.05 | 6 | 25 g |
| residue | | | 27 g |
| | | | 360 g |
| | | | ≏ 98% of theory |

| Analysis: | | calculated | found |
|---|---|---|---|
| n = 3 | % C | 56.02 | 55.86 |
| | % H | 7.44 | 7.44 |
| | % N | 5.44 | 5.76 |
| n = 4 | % C | 55.80 | 54.64 |
| | % H | 7.69 | 7.69 |
| | % N | 4.65 | 4.71 |
| n = 5 | % C | 55.64 | 55.49 |
| | % H | 7.88 | 7.88 |
| | % N | 4.05 | 4.10 |

[1]commencing decomposition

The NMR spectrum confirms the structures.

EXAMPLE 3

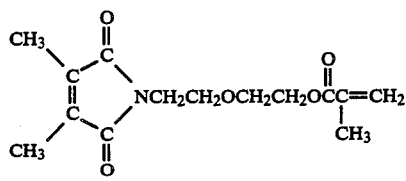

106.6 g (0.5 mol) of the dimethylmaleinimidyl alcohol from Example 1 are placed into 250 ml of toluene in a three-necked flask fitted with mechanical stirrer, water separator and thermometer, and 47.34 g (0.55 mol) of methacrylic acid, 120 mg of di-tert-butyl-p-cresol and 3 ml of sulfuric acid are added. The mixture is refluxed for 2 hours, and about 8.8 ml of water are separated. After cooling of the mixture in an ice-bath, 100 ml of petroleum ether are added, and the mixture is stirred twice with water, once with sodium hydroxide solution (1N) and again twice with water. The colourless toluene solution is concentrated in a rotary evaporator to thus obtain, after removal of the solvent residues under high vacuum, 116 g of polymer-free crude product (83% yield, 98% purity), which can be used for polymerisation, without distillation. The product distills at 140°–142° C., 0.05 mm/Hg.

| Analysis: | calculated | found |
|---|---|---|
| % C | 59.78 | 59.68 |
| % H | 6.81 | 6.64 |
| % N | 4.98 | 4.94 |

The NMR spectrum is in agreement with the structure.

The higher homologous compounds given in Table 1, with n=3, 4 and 5, are produced by the same process from the corresponding alcohols of Example 2.

TABLE 1

| | Yield | 3.6 ppm | | 4.3 ppm |
|---|---|---|---|---|
| n = 3 | 80% | 10 protons | | 2 |
| 4 | 76% | 14 protons | | 2 |
| 5 | 72% | 18 protons | | 2 |

EXAMPLE 4

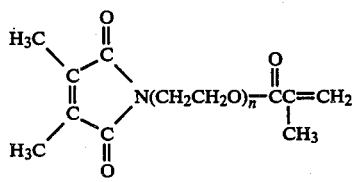

(mixtures of homologous compounds with n=2, 3, 4, etc.)

106 g (0.5 mol) of dimethylmaleinimidyl alcohol according to Example 1 are placed into a three-necked flask, fitted with stirrer, water separator and thermometer, and dissolved in 250 ml of toluene. There are then added 2 ml of boron trifluoride etherate, and 22 g (0.5 mol) of ethylene oxide are introduced at 70° C. with vigorous stirring in the course of 20 minutes. The alcohol mixture thus obtained is esterified, in a manner analogous to that of Example 3, with methacrylic acid. The result after isolation is 135 g of polymer-free product (80% yield), which can be used directly for polymerisation. According to the thin-layer chromatogram and gas chromatogram, the product is a mixture of compounds with principally n=2, 3, 4, 5 and 6.

It is possible in an analogous manner to produce, by variation of the added amount of ethylene oxide, various mixtures of homologues, which vary from each other in their hydrophilic behaviour.

Polymerisation Examples

EXAMPLE 5

Into a 500 ml double-walled reaction vessel, provided with heating, stirrer, thermometer, dropping funnel, condenser and $N_2$-connection, are placed:

| | |
|---|---|
| 48.75 g | of dimethylimidylmethacrylate from Example 3 (not distilled) (65%) |
| 15 g | of methylmethacrylate (20%) |
| 11.25 g | of methacrylic acid (15%) |
| 291 g | of a 1:1 mixture (volume ratio) of methyl cellosolve (MCS) and methyl ethyl ketone (MEK). |

A solution of 450 mg of $\alpha,\alpha'$-azo-isobutyronitrile (AIBN) in 9 g of the same solvent mixture is placed into the dropping funnel. The apparatus is evacuated three times, flushed with nitrogen, and then kept under a nitrogen excess pressure. The reaction mixture is heated to 65° C., and ⅓ of the AIBN solution is added. After five hours and after 10 hours, there is added in each case a further third of the AIBN solution. The polymer solution is cooled after a reaction time of 22 hours. Ether is added to the viscous colourless polymer solution, and the precipitated solid polymer is filtered off and dried.

The polymer yield is about 95%.

The inherent viscosity is 0.263 dl/g (0.5% in MCS at 25° C.). The acid content is determined by titration and is 14.9%).

In Table 2 are listed further polymers which are produced in a manner analogous to that described above.

TABLE 2

| No. | Employed monomer mixture (% by weight) | Concentration of polymerisation solution in % by wt. | Intrinsic viscosity | Acid content % | Yield % |
|---|---|---|---|---|---|
| 1 | monomer from Example 3 75% | 15% | 0.18 | 13.9 | 94 |

TABLE 2-continued

| No. | Employed monomer mixture (% by weight) | Concentration of polymerisation solution in % by wt. | Intrinsic viscosity | Acid content % | Yield % |
|---|---|---|---|---|---|
| | methylmethacrylate 10% methacrylic acid 15% | | | | |
| 2 | monomer from Example 3 65% methylmethacrylate 20% methacrylic acid 15% | 15% | 0.19 | 14.6 | 95 |
| 3 | monomer from Example 3 90% methacrylic acid 10% | 15% | 0.18 | — | 94 |
| 4 | monomer from Example 3 50% methylmethacrylate 30% methacrylic acid 20% | 15% | 0.25 | 18.9 | 90 |
| 5 | monomer from Example 3 85% methacrylic acid 15% | 15% | 0.18 | — | 96 |
| 6 | monomer from Example 3 80% methacrylic acid 20% | 15% | 0.22 | — | 95 |
| 7 | monomer from Example 3 60% ethylacrylate 20% methacrylic acid 20% | 15% | 0.22 | — | 86 |
| 8 | monomer from Example 3 65% methylmethacrylate 20% methacrylic acid 15% | 25% | 0.30 | 14.2 | 94 |
| 9 | monomer from Example 3 65% methylmethacrylate 20% methacrylic acid 15% | 30% | 0.40 | 14.8 | 95 |
| 10 | monomer from Example 3 90% methacrylic acid 10% | 30% | 0.33 | — | 95 |
| 11 | monomer mixture from Example 4 (1.5 equiv. of ethylene oxide) 65% methylmethacrylate 20% methacrylic acid 15% | 20% | 0.35 | 16 | 90 |
| 12 | monomer mixture from Example 4 (1.0 equiv. of ethylene oxide) 65% methylmethacrylate 20% methacrylic acid 15% | 20% | 0.27 | 16.7 | — |
| 13 | monomer mixture from Example 4 (1.0 equiv. of ethylene oxide) 95% methacrylic acid 5% | 20% | 0.24 | 5.4 | 18 |
| 14 | monomer from Example 3 70% 4-vinylpyridine 30% | 20% | 0.18 | — | 70% soluble in 1NHCl |
| 15 | monomer from Example 3 50% 1-vinyl-2-pyrrolidone 50% | 20% | 0.12 | — | 55 |
| 16 | monomer from Example 3 70% 1-vinyl-2-pyrrolidone 30% | 20% | 0.14 | — | 80 |

Application Examples

EXAMPLE 6

The polymer solution, produced as in Example 5, is diluted with the solvent mixture, methyl cellosolve/methyl ethyl ketone (1:1) to give a solid content of 7%. Under yellow light is added 8% of a thioxanthone sensitiser, relative to the solid content,

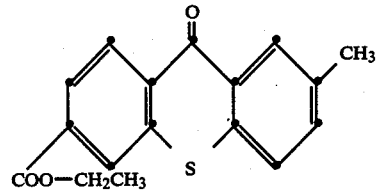

as well as commercial matting and levelling agents.

The polymer solution is then applied, by means of a coating machine, to a 100μ thick polyester sheet, and is dried at 110° C. The layer thickness corresponds to a polymer application of 3 g/m². The film produced in this manner is irradiated, through an image mask, for 20 seconds with a 1000 W metal halide lamp at a distance of 80 cm. Development is then performed at 40° C. in a 5% sodium carbonate solution, and the resulting polymer relief is washed with water at room temperature. It is subsequently coloured with an aqueous solution of commercial Maxilon dyes, and the film is dried after the excess dye has been removed by washing.

The optical density of the treated film is in the wavelength range of 350–500 nm ≧ 3.

EXAMPLE 7

There are produced, with the polymer solution used in Example 6, films of different applied amounts of polymer: 2.8, 3.0, 3.3 and 3.9 g/m². The films are then developed, after image-wise exposure, with a 5% sodium carbonate solution using different contact times during development and and varying bath temperatures. The results are shown in the following Table 3.

TABLE 3

| Bath temperature | Contact time during development | | | |
|---|---|---|---|---|
| | 15 sec. | 18 sec. | 25 sec. | 38 sec. |
| 40° C. | good | good | good | good |
| 35° C. | fog | good | good | good |

TABLE 3-continued

| Bath tempera-ture | Contact time during development | | | |
|---|---|---|---|---|
| | 15 sec. | 18 sec. | 25 sec. | 38 sec. |
| 30° C. | fog | fog | fog | good |

In various layer thicknesses, the polymer can be developed within wide limits with respect to temperature and contact time during development.

The analogous polymer with comparable viscosity and acid content but containing the next lower homologous monomer according to Example 3 (n=1) cannot be developed in sodium carbonate solution. When the acid content is increased to 20%, so that the polymer becomes soluble under the applied conditions, the contact-time tolerance is very small (≦5 sec.).

The advantage of the described polymer is the good adhesion of the polymer layer in the case of aqueous-/alkaline development, and the good and rapid solubility of the unexposed polymer. The improvement in adhesion is shown particularly with thicker layers.

EXAMPLE 8

The polymer solution produced in Example 5, Table 2, is sensitised with 5% of sensitiser (analogously to Example 6), and 0.25% of Ovasolrot B (red) and 0.5% of di-tert-butyl-p-cresol are added. An aluminium plate is coated with the solution thus obtained and is subsequently dried at 80° C. for 3 minutes. The applied amount of polymer corresponds to about 3 g/m². The resulting printing plate is irradiated with a 1000 W metal halide lamp, at a distance of 80 cm, for 20 seconds through a mask; it is afterwards developed in a 1% sodium carbonate solution for 1-2 minutes and washed with water. After brief immersion in 1% phosphoric acid, the polymer relief is coloured with a printing paste.

EXAMPLE 9

To the polymer solution from Example 5, table 2, No. 11, are added 2% of sensitiser (cp. Example 6) and 0.2% of Ovasolrot B. A printed circuit board is coated with this polymer solution, and subsequently dried at 85° C. for 25 minutes. The applied layer thickness corresponds to a polymer applied amount of 32 g/m². The printed circuit board is irradiated image-wise with a 1000 W metal halide lamp for 100 seconds at a distance of 80 cm, and is subsequently developed at 30° C. in a 1% sodium carbonate solution for 1.5 minutes. There is formed a well-adhering polymer relief, onto which copper can be deposited in a galvanising bath.

What is claimed is:

1. A photosensitive, crosslinkable homopolymer, having a molecular weight of 1000 to 1,000,000, as measured by the viscosity of a 0.5% by weight solution in methyl cellosolve at 25° C., prepared by the polymerization of an imidyl compound of formula I

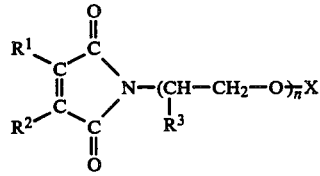

wherein
- $R^1$ and $R^2$ independently of one another are $C_1$–$C_4$-alkyl, or
- $R^1$ and $R^2$ together are tetramethylene,
- $R^3$ is a hydrogen atom or normal $C_1$–$C_4$-alkyl,
- n is a number from 2 to 30, and
- X is —CO—$CR^4$=$CH_2$, in which $R^4$ is a hydrogen atom or methyl.

2. A polymer according to claim 1 where in formula I $R^1$ and $R^2$ are each methyl, $R^3$ is hydrogen, n is 2 and X is methacryloyl.

3. A photosensitive, crosslinkable copolymer, having a molecular weight of 1000 to 1,000,000, as measured by the viscosity of a 0.5% by weight solution in methyl cellosolve at 25° C., which comprises the polymerization product of
   (a) 1 to 99% by weight, based on the total copolymer, of an imidyl compound of formula I

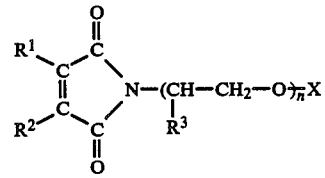

wherein
- $R^1$ and $R^2$ independently of one another are $C_1$–$C_4$-alkyl, or
- $R^1$ and $R^2$ are tetramethylene,
- $R^3$ is a hydrogen atom or normal $C_1$–$C_4$-alkyl,
- n is a number from 2 to 30, and
- X is —CO—$CR^4$=$CH_2$, in which $R^4$ is a hydrogen atom or methyl, and
   (b) 99 to 1% by weight, based on the total copolymer, of an ethylenically unsaturated comonomer.

4. A copolymer according to claim 3 wherein the unsaturated comonomer is a vinyl monomer.

5. A copolymer according to claim 4 wherein the vinyl monomer is acrylic acid, methacrylic acid, an acrylate ester, a methacrylate ester or mixture thereof.

6. A copolymer according to claim 5 wherein the copolymer comprises the polymerization product of
   (a) 40 to 90% by weight, based on the total copolymer, of a compound of formula I,
   (b) 30 to 5% by weight, based on the total copolymer, of acrylic acid or methacrylic acid, plus 30 to 5% by weight, based on the total copolymer, of an acrylate ester or a methacrylate ester.

7. A copolymer according to claim 6 wherein, based on the total copolymer,
   (a) is 60 to 90% by weight of a compound of formula I, and
   (b) is 20 to 5% by weight of acrylic acid or methacrylic acid, plus 20 to 5% by weight of an acrylate ester or a methacrylate ester.

8. A copolymer according to claim 3 where in formula I $R^1$ and $R^2$ are each methyl, $R^3$ is hydrogen, n is 2 and X is methacryloyl.

* * * * *

UNITED STATES PATENT AND TRADEMARK OFFICE
CERTIFICATE OF CORRECTION

PATENT NO. : 4,629,773
DATED : DECEMBER 16, 1986
INVENTOR(S) : BEAT MÜLLER

It is certified that error appears in the above-identified patent and that said Letters Patent is hereby corrected as shown below:

Column 12, Claim 3, Line 39, "$R^1$ and $R^2$ are tetramethylene," should read --$R^1$ and $R^2$ together are tetramethylene, --.

Signed and Sealed this

Eighth Day of September, 1987

Attest:

DONALD J. QUIGG

Attesting Officer     Commissioner of Patents and Trademarks